United States Patent [19]
Davila et al.

[11] Patent Number: 6,059,111
[45] Date of Patent: May 9, 2000

[54] MEDICAL DEVICE PACKAGING SYSTEM

[75] Inventors: James M. Davila, Corona; Hai Parson, Aliso Veijo, both of Calif.

[73] Assignee: Medtronic, Inc., Minneapolis, Minn.

[21] Appl. No.: 09/262,649

[22] Filed: Mar. 4, 1999

Related U.S. Application Data

[60] Provisional application No. 60/076,766, Mar. 4, 1998.

[51] Int. Cl.[7] .................................................. A61B 17/06
[52] U.S. Cl. ........................................... 206/438; 206/497
[58] Field of Search .................................... 206/363, 438, 206/526, 564, 570, 497; 53/399, 442

[56] References Cited

U.S. PATENT DOCUMENTS

| | | | |
|---|---|---|---|
| 3,153,505 | 10/1964 | Bessett | 206/497 |
| 3,851,649 | 12/1974 | Villari | 206/438 |
| 3,918,584 | 11/1975 | Richardson | 206/497 |
| 4,018,904 | 4/1977 | Muraoka | 206/497 |
| 4,257,211 | 3/1981 | Fales et al. | 53/442 |
| 4,306,653 | 12/1981 | Fales | 206/326 |
| 4,540,399 | 9/1985 | Litzie et al. | 607/4 |
| 4,697,703 | 10/1987 | Will | 206/438 |
| 4,736,850 | 4/1988 | Bowman et al. | 206/438 |
| 4,750,619 | 6/1988 | Cohen et al. | 206/438 |
| 4,850,954 | 7/1989 | Charvin et al. | 604/4 |
| 5,117,981 | 6/1992 | Crawford et al. | 206/438 |
| 5,163,554 | 11/1992 | Lampropoulos et al. | 206/363 |
| 5,392,918 | 2/1995 | Harrison | 206/438 |
| 5,405,005 | 4/1995 | White | 206/363 |
| 5,441,707 | 8/1995 | Lewis et al. | 206/438 |
| 5,540,653 | 7/1996 | Schock et al. | 604/7 |
| 5,543,606 | 8/1996 | Gies | 219/730 |
| 5,735,404 | 4/1998 | Kumakura et al. | 206/497 |
| 5,868,253 | 2/1999 | Krueger et al. | 206/363 |

FOREIGN PATENT DOCUMENTS

| | | | |
|---|---|---|---|
| 0 283 145 A2 | 9/1988 | European Pat. Off. | B65D 81/34 |
| 0 369 084 A1 | 11/1988 | European Pat. Off. | B65D 5/50 |
| 2 263 170 | 7/1974 | France | B65D 85/30 |
| 2 677 961 | 12/1992 | France | B65D 85/42 |
| 25 35 712 | 9/1975 | Germany | B65D 11/00 |
| 197 20 244 A1 | 11/1997 | Germany | B65D 71/06 |

*Primary Examiner*—David T. Fidei
*Attorney, Agent, or Firm*—Harold R. Patton

[57] ABSTRACT

A system and method for packaging devices, preferably medical devices that are arranged together and/or require sterilization, that permits the devices to be held to a removable insert (such as a tray) by conventional "shrink-wrap" film. as opposed to a "band" or "belt" of non-shrinkable material that surrounds (in part) the device and is affixed in some manner to the inside surfaces of a container. The removable insert is suspended above the floor of an outer tray, thus the shrink-wrap film may encircle the insert and hold the device(s) in place upon shrinkage of the film.

15 Claims, 5 Drawing Sheets

MEDICAL DEVICE PACKAGING SYSTEM

CROSS-REFERENCE TO RELATED APPLICATION

This application claims the benefit of provisional application No. 60/076,766 filed Mar. 4, 1998.

TECHNICAL FIELD

This invention relates to a system and method for packaging objects such as medical devices.

BACKGROUND

Many types of medical devices are arranged with, connected to, or otherwise packaged with other devices prior to shipment to the end user. Optionally, individual devices or combinations of devices may need to be sterilized prior to shipment. In either case, and especially when both situations are present together, the packaging which contains the device(s) must maintain the arrangement and sterility, or both, of the contents of the package. Examples of packaging systems for medical devices include the following US patents, each of which is incorporated into this application by reference in its entirety: U.S. Pat. Nos. 4,540,399 (Litzie et al.); 5,540,653 (Schock et al.); 5,163,554 (Lampropoulos et al.); and 4,850,954 (Charvin).

DISCLOSURE OF THE INVENTION

One aspect of the invention is a container system for packaging medical devices, comprising an inner organizing tray; an outer tray having a floor and a means to suspend the inner organizing tray within and above the floor of the outer tray; and at least one device located on the inner organizing tray. The inner organizer tray is encircled with at least one band of shrink-wrap material. The encircled inner organizer tray is then suspended above the floor of the outer tray, and the shrink-wrap film is shrunken around at least one device.

Another aspect of the invention is a method of packaging medical devices, comprising the steps of providing an inner organizing tray, and an outer tray having a floor and a means to suspend the inner organizing tray within and above the floor of the outer tray; locating at least one device on the inner organizing tray; encircling the inner organizer tray with at least one band of shrink-wrap material; placing the encircled inner organizer tray within and suspended above the floor of the outer tray; and shrinking the shrink-wrap film around at least one device.

DETAILED DESCRIPTION

Figure 1:
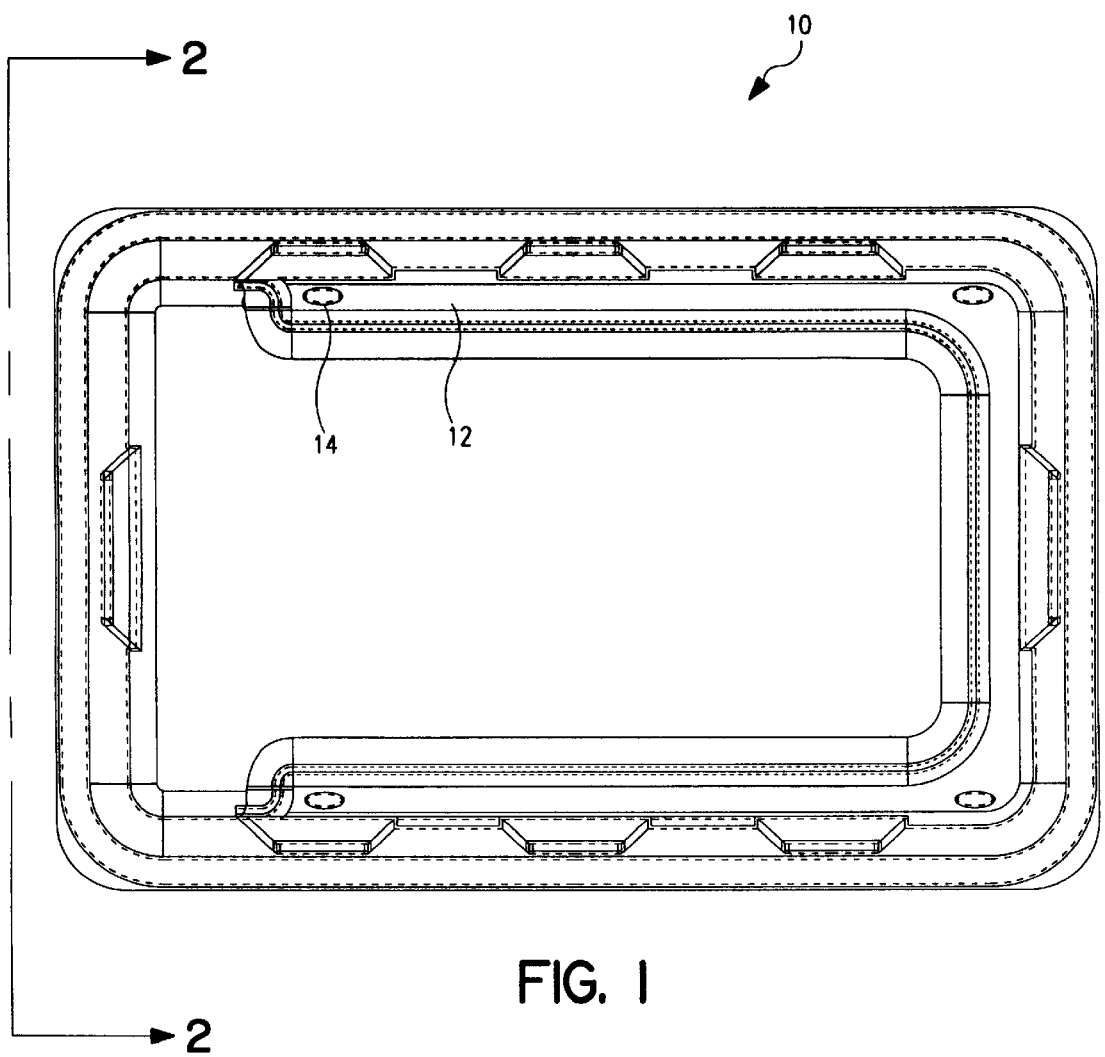
FIG. 1 is a top view of the outer tray portion of an embodiment of the invention.

The invention is a system and method for packaging medical devices that permits the devices to be held to a removable insert (including but not limited to a tray in which the devices are placed) by conventional "shrink-wrap" film. The preferred film is any conventional heat-shrinkable film (or functionally equivalent materials), and especially polyolefin, but films of other materials, or films shrinkable by other means, are potentially suitable for use with the invention. Thus, in general, any material which has the functional property of shrinking upon application of an external agent is included in the term "shrink-wrap film" as such term is used in this application and the appended claims.

Conventional practice is to hold a device in place with a "band" or "belt" of non-shrinkable material that surrounds (in part) the device and is affixed in some manner to the inside surfaces of a container. There is one band per device. The bands produce tension only along their length, which holds the device in only one direction, i.e., toward the inside surface of the container. The device is prone to lateral movement, i.e., "slipping out of the belt."

In the invention, at least one band of "shrink-wrap" material encircles at least one medical device which has been placed on a inner organizer tray. The inner organizer tray is then placed within an outer tray. The outer tray comprises a notch or ledge or any other suitable means for suspending the inner organizer tray above the floor of the outer tray. This ensures that the "shrink-wrap" film may encircle the inner organizer tray and thus hold the medical device(s) to the organizer tray upon shrinkage. If the device or devices were placed in conventional supports on the bottom of the outer tray, the "shrink-wrap" film would not be able to encircle the device and thus upon shrinkage it would not hold the device in place. The "shrink-wrap" film holds the devices to the inner organizer tray in all directions because it is tightly shrunk into compliance with the devices and inner organizer tray.

Suspension of the inner organizer tray above the floor of the outer tray also provides an intermediate space where, optionally, other devices may be located.

The number and identity of devices located in the inner organizer tray and the intermediate space are both arbitrary. Typical cases include, but are not limited to, devices used in procedures such as kidney dialysis, hemodialysis, hemoultrafiltration, and blood oxygenation; but in general, any medical device may benefit from the advantages of the invention.

At least one band of "shrink-wrap" film is provided for at least one device. Thus, the following configurations are within the scope of the invention:

1. A plurality of medical devices held by a single band of "shrink-wrap" film.
2. A single medical device held by a plurality of bands of "shrink-wrap" films.
3. A plurality of medical devices held by plurality of bands of "shrink-wrap" films; the number of devices need not necessarily equal the number of bands.
4. At least one medical device completely surrounded by a closed "sphere" (as adjusted by the shape of the inner organizer tray and device(s) upon shrinkage) of "shrink-wrap" film.
5. At least one medical device encircled by a "cylinder" (as adjusted by the shape of the inner organizer tray and device(s) upon shrinkage) of "shrink-wrap" film. The "cylinder" may be open at one or both ends. The preferred embodiment of the invention uses such a "double open ended" configuration, so that ETO sterilization may be more effective, and also because it allows the inner organizer tray to be located at one extreme end of the outer tray. This arrangement provides the greatest amount of access to the end of the inner organizer tray which is "open" within the outer tray. It also permits additional devices to be added to the collection of devices within the entire system. For example, a "softshell" venous reservoir is a type of medical device which, due to properties of the material from which it is constructed, is not preferably exposed to the heat of a "shrink-wrap" operation. (Some types of "softshell" reservoirs are constructed of a transparent material that becomes undesirably wrinkled or deformed upon exposure to heat. Such devices can be sterilized separately and then added to the system through the open ended cylinder of shrunken "shrink-wrap" material, or they can be placed outside of the "shrink-wrap" material.)

In any embodiment, if possible "finger holes" could be provided in the "shrink-wrap" film so that, upon removal of the inner organizer tray from the other tray, the "shrink-wrap" film may be easily removed by inserting at least one finger in a finger hole and ripping the film.

Also, in any embodiment, an optional feature is a rigid lid that may be permanently sealed over the outer tray once the contents have been removed, used, and returned. This feature is especially preferred where the used contents are subject to contamination or to themselves act as contaminants after their intended use. For example, if the contents contact human blood during normal use, they must be properly sealed and disposed of after use. In the preferred embodiment, a bead of pressure sensitive adhesive is positioned in a channel formed into the lid so as to engage (preferably but not necessarily by interference fit and/or perimeter snap features) the top edge of the sealing flange and/or wall(s) of the outer tray. Thus, the contents are sealed inside upon application of pressure to the lid. A sufficient amount of conventional adhesive should be used to create a hermetic seal upon application of reasonable amounts of pressure. Other conventional adhesive systems could be used in place of the preferred pressure sensitive adhesive system just described. A release liner to protect the adhesive may be used, but the preferred embodiment uses an exposed adhesive.

Conventional "shrink-wrap" materials and equipment may be used with the invention. For example, preferred equipment includes the RENNCO REWRAP Model 3618-120 Sleeve Wrapper; the Watlow Series 935 Heat Controller, the BELCO Model ST 3010 Shrink Tunnel, and conventional auxiliary equipment. The preferred process uses conventional "double roll" techniques, in which two separate rolls of material are used to introduce films above and below the medical device subassembly, followed by thermal bonding of the two films at their mutual outer edges (corresponding to the longitudinal direction as the material comes off the roll).

It is also contemplated that the inner organizer tray my be configured as a cassette that would mount on a equipment support platform such that the pre-assembled components were immediately arranged for use without separate installation onto ancillary support equipment.

EXAMPLE

An embodiment of the invention is adapted for packaging of sterilized extracorporeal circuits, i.e., devices and tubing used to remove a bodily fluid from the body, pass the fluid into special purpose devices, and return the fluid to the body. For example, a preferred embodiment of this invention is the Medtronic STAT-PAC (Medtronic Perfusion Systems, Minneapolis, Minn. USA), which is shown in a two-page advertising brochure entitled "High Performance Package. Introducing The Medtronic STAT-PAC," Medtronic document number UC9800819EN, dated 1998. It is believed that this brochure was published for the first time on Mar. 6, 1998. (The embodiment shown in the brochure did not employ a lid with an adhesive as described above.).

A common extracorporeal bypass circuit includes devices such as kinetic pumps, mass transfer devices, filters, reservoirs, and heat exchangers. (Some of these components may be incorporated into the design of other of the components. For example, a mass transfer device may have an integral heat exchanger, reservoir, filter, or a combination of any or all of them.) In the case of an extracorporeal blood circuit suitable for heart-lung bypass surgery and/or blood processing systems and diagnostic hemostasis management systems, the devices may be bubble or membrane oxygenators, arterial filters, cardiotomy reservoirs, bubble separators, blood heat exchangers, red blood cell washers, or pumps of any suitable type. Other types of blood management systems employ extracorporeal blood circuits. Thus, the invention is suitable for packaging one or more of any of these types devices, both when they are incorporated into an extracorporeal bypass circuit, and when such devices are used outside the context of extracorporeal bypass (e.g., blood in coagulation testing systems, cell culture media, cell suspensions, proteins, and microcapsule suspensions).

Optionally, a "table pack" may include pre-bypass filters, suction wands, cannula, and the like. In a preferred embodiment, a "table pack" of tubing is located in the intermediate space, and is also optionally within the encircling "shrink-wrap" film and thus held in place against the inner organizer tray. Considering as an example the devices and tubing used in cardiac bypass procedures, this arrangement permits conventional separate assembly of the "pump pack" and "table pack." The devices in the "pump pack" are connected to the tubing and devices in the "table pack," and the length of tubing interconnecting the devices simply wraps around the end of the inner organizer tray from the upper side to the lower (intermediate space) side.

Coiled tubing is preferably held within an arrangement comprising two sheets of "surgical wrap" material thermally sealed along their sides. A preferred material is available from Kimberly-Clark Corporation under the tradename "SPUNGUARD One Step Regular Sterilization Wrap" model numbers 12709 00 (9×9 inches) and 12712 00 (12×12 inches). (It appears that the tradename KIMGUARD may also be used with the same or functionally equivalent products.) This material is porous and suitable for conventional sterilization processes using ethylene oxide (ETO) as well as aseptic handling of the coiled tubing. Other materials that hold the coiled tubing in place are suitable, such as non-bonded individual sheets, pre-formed containers, etc.

Figure 2:
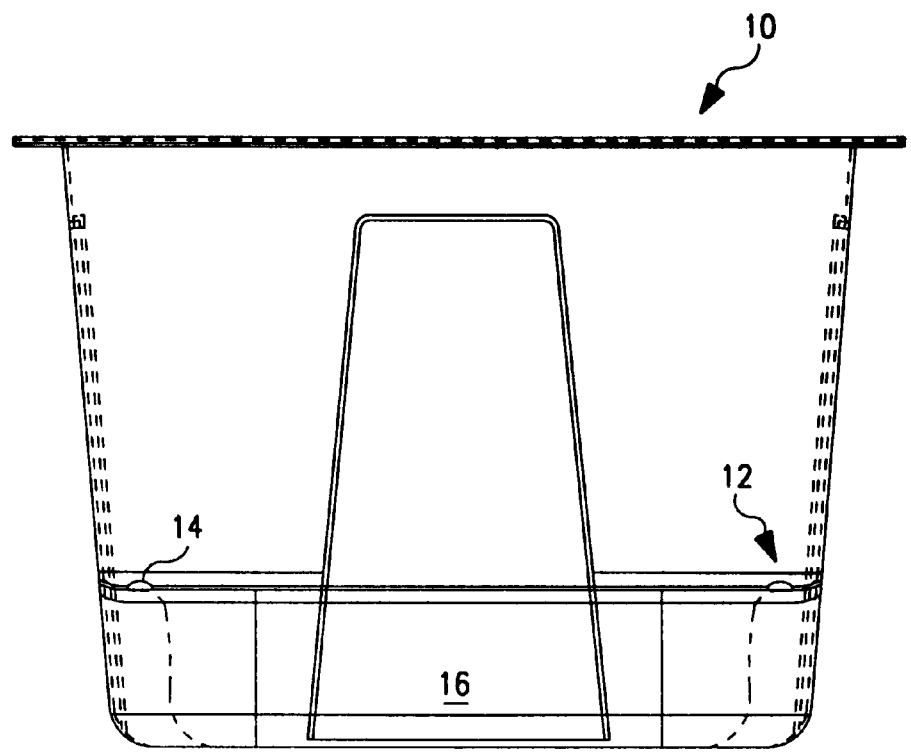
FIG. 2 is a side view taken along the line 2—2 of FIG. 1

FIGS. 1 and 2 show a preferred embodiment of the outer tray of the invention. Neglecting minor features not critical to the definition or operation of the invention, it may be said that the outer tray 10 is a generally rectangular open box having four sloping walls and a floor. A generally U-shaped 12 ledge is incorporated into three of the walls (an embodiment in which only two opposite walls incorporated the ledge is possible but not preferred because the three wall design provides greater support for the inner organizer tray, and also provides space for tubing connections to the intermediate space). Located on the ledge 12 are four raised anchors such as the example anchor designated as 14. Each of these anchors will match up with a mating opening on the inner organizer tray, as discussed below. The preferred material for the outer tray 10 is 0.177-inch thick high impact polystyrene (HIPS), having 5% to 7% rubber (butadiene) additive, tinted white or equivalent. In this embodiment, because of the dimensions (especially the draft) of the outer container, the cavity formed beneath the anchors 14 when they are formed in the outer container 10 must be filled with epoxy or similar material to ensure that the anchors 14 have sufficient strength to perform their task. A suitable epoxy is a 1:1 blend of Lord 305-1 resin and Lord 305-2 hardener.

Figure 4:
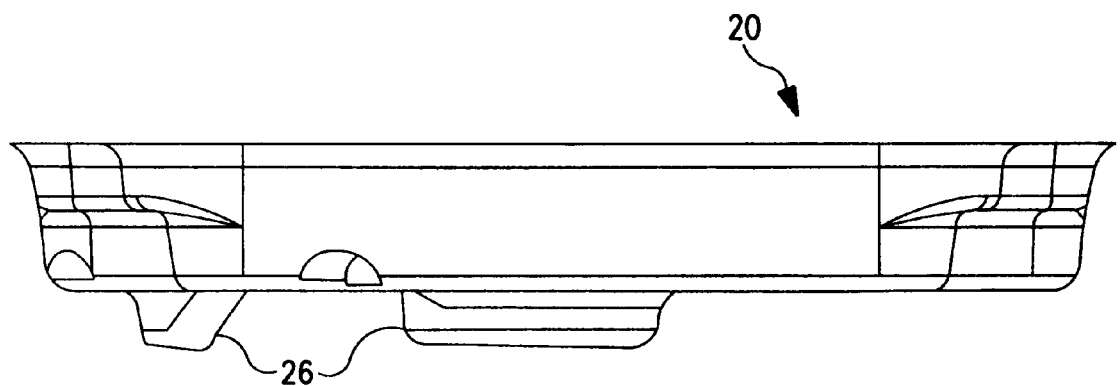
FIG. 4 is a side view taken along the line 4—4 of FIG. 3.
Figure 3:
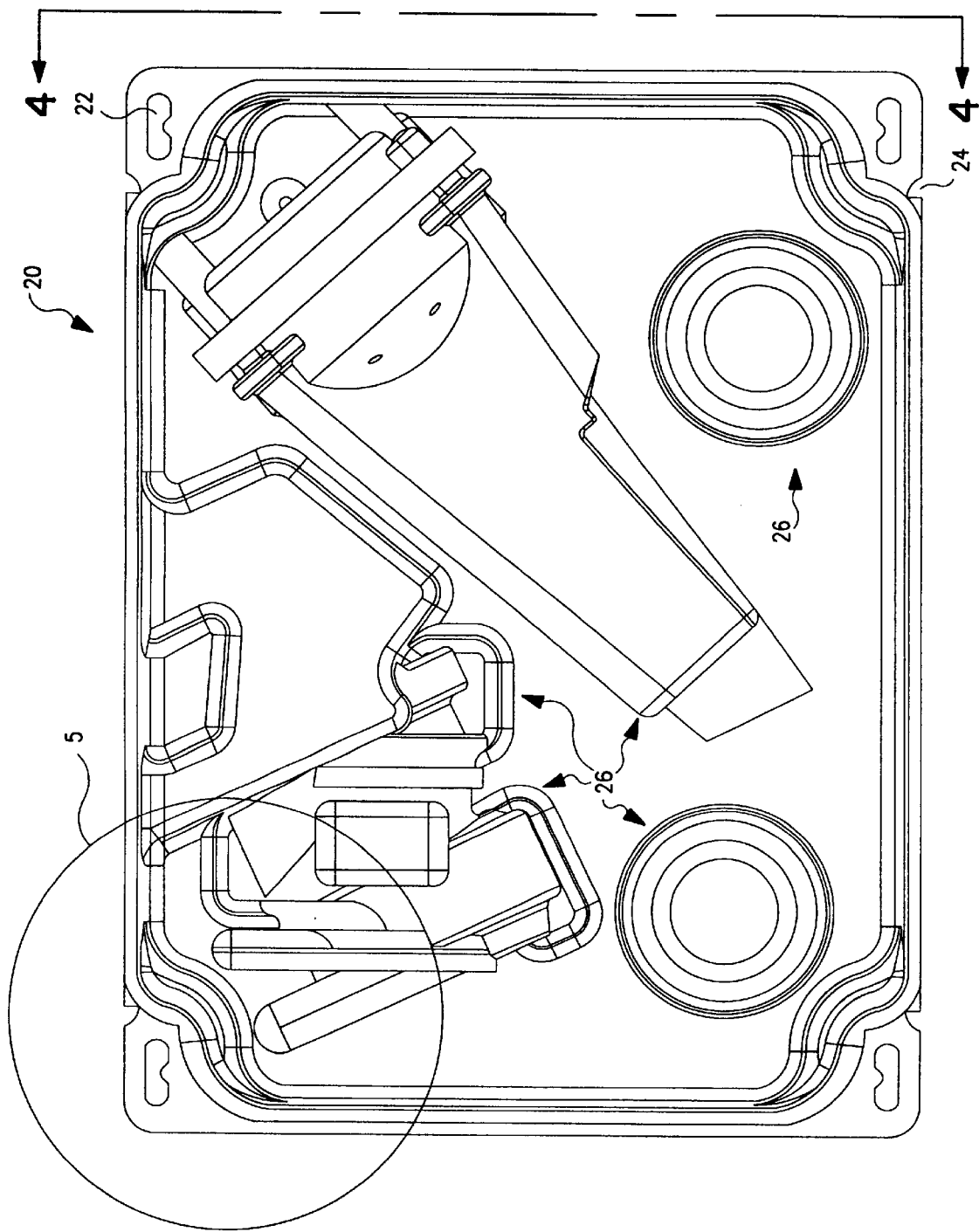
FIG. 3 is a top view of the inner organizing tray portion of an embodiment of the invention.
Figure 5:
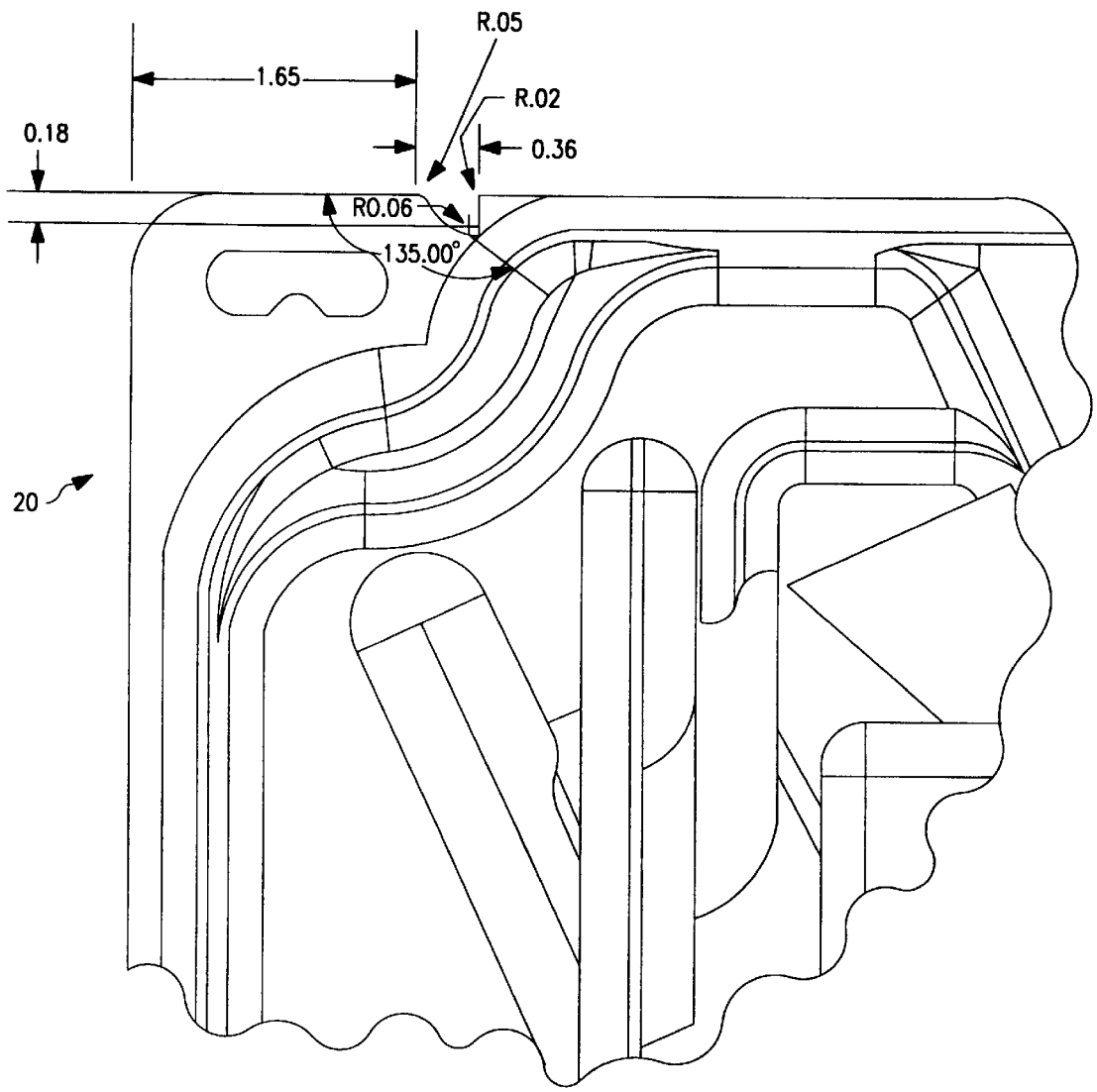
FIG. 5 is an enlarged view of the indicated portion of FIG. 3.

FIGS. 3, 4 and 5 show a preferred embodiment of the inner organizer tray 20 of the invention that is designed for insertion into the outer tray 10 of FIGS. 1 and 2. As shown, each corner of the generally rectangular inner organizer tray has an opening 22 that is designed to mate with the raised anchor 14 of the outer tray 10. In the preferred embodiment, raised anchor 14 and opening 22 are each generally oval in shape, although opening 22 has a small tab that improves the frictional lock between it and raised anchor 14.

Various features 26, typically depressions, are molded into inner organizer tray 20 to hold the device(s) (not shown) placed onto the tray. These features 26 are determined by the exact configuration of the specific devices, and thus are not critical to defining the full scope of the invention. Note that the depth of the features is preferably less than the height of the ledge 12 above the floor of the outer tray 10 so that there is an intermediate space 16 (see FIG. 2) below the suspended inner organizer tray 20 and the floor of the outer tray 10.

The preferred material for the inner organizer tray 20 is 0.075-inch thick high impact polystyrene (HIPS), having 5% to 7% rubber (butadiene) additive, white.

FIG. 5 shows specific dimensions and configuration of a preferred embodiment of the removable inner organizer tray 20. All dimensions are preferred but not required, and are shown to indicate relative proportions that are preferred in the invention. Note particularly the notch 24 which is typical of each corner of the inner organizer tray 20. The notch 22 is generally shaped to present an asymmetric opening into the tray which is obliquely angled away from the generally elliptical hole 22 near the corner of the tray (and thus acutely angled with respect to the major portion of the side of the tray). The notch 24 is generally straight on one side; on the other side, it has a semicircular portion which begins at the most inward portion of the notch and ends at a smaller generally straight portion which continues to the side of the tray. There is a minimally slight radius at the intersection of the semicircular portion and the smaller generally straight portion. The slight radius should be chosen such that conventional "shrink-wrap" film is held in place during conventional shrinkage of the film. The semicircular shape is preferred but not required.

The particular arrangement of the notch 24 is designed to accomplish the following objectives. First, the notch 24 must generally hold the "shrink-wrap" film (not shown) in place during the shrinkage of the film so that the film will shrink primarily in the circumferential direction around the upper and lower sides of the inner organizer tray (and thus shrink around and down onto the device or devices on the inner organizer tray). The oblique angle that the notch makes with the corner portion of the inner organizer tray means that the shrinking film must "work uphill" to pull out of the notch; thus, the dimensions and shape of the notch are selected to resist this movement of the shrinking film to a degree sufficient for the film to remain generally in place throughout the shrinking process. The rounded "J-hook" portion of the notch is designed to present a longer distance for the shrinking edge of the film to travel. The edges of the features of the notch are radiused to prevent the film from being cut during shrinkage and subsequent handling.

Any feature on the inner organizer tray which achieves these objectives is considered to be equivalent to the preferred notch shown.

Figure 6:
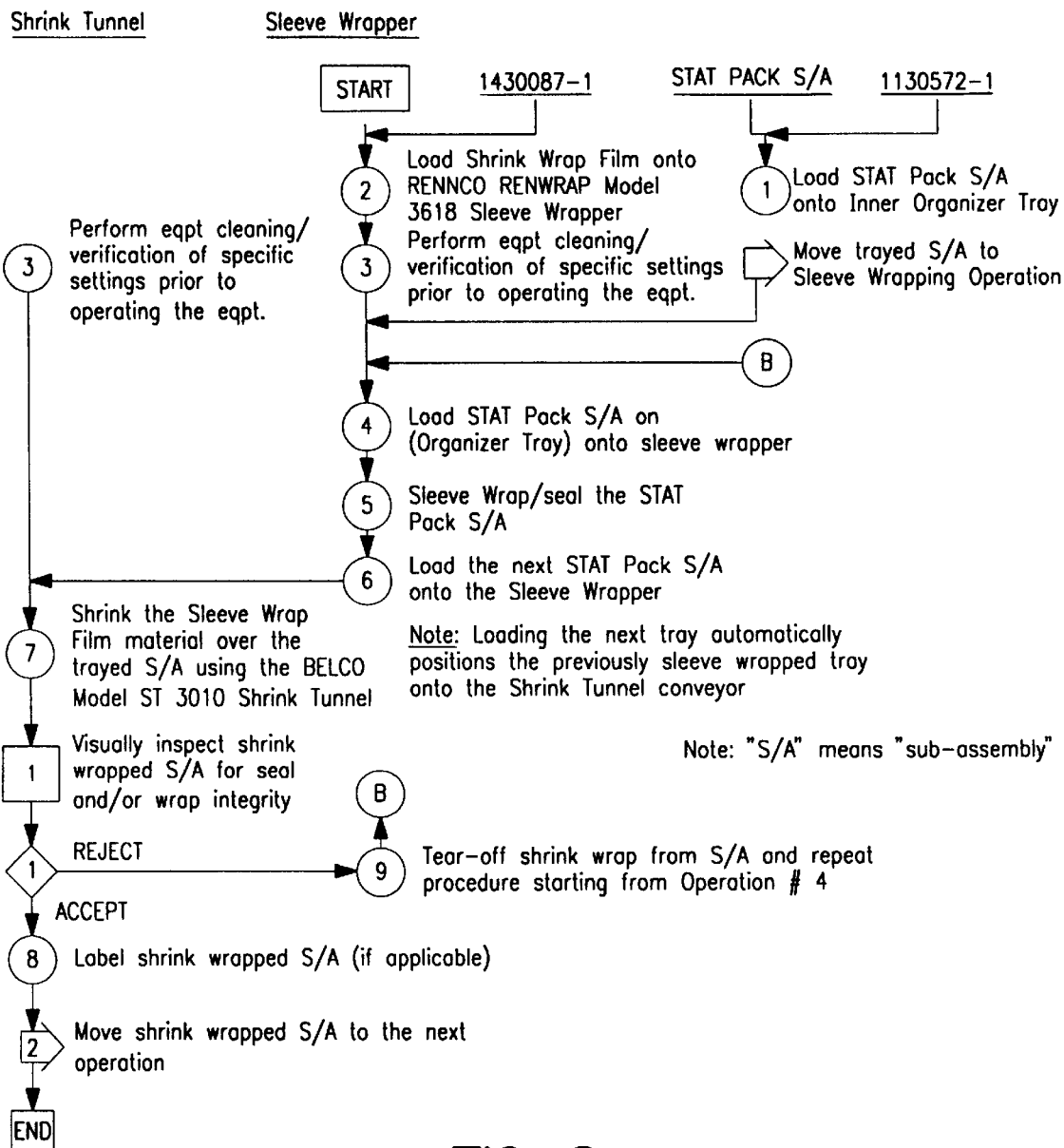
FIG. 6 is a process flow chart for the procedure used to install shrink wrap material into an embodiment of the invention.

FIG. 6 shows the general process of installing the "shrinkwrap" material, using the preferred RENNCO REWRAP Model 3618-120 Sleeve Wrapper; the Watlow Series 935 Heat Controller, the BELCO Model ST 3010 Shrink Tunnel, and conventional auxiliary equipment. This preferred process uses conventional "double roll" techniques, in which two separate rolls of material are used to introduce films above and below the medical device subassembly, followed by thermal bonding of the two films at their mutual outer edges (corresponding to the longitudinal direction as the material comes off the roll).

We claim:

1. A container for at least one device, comprising an inner organizing tray, an outer tray having a floor and a means to suspend the inner organizing tray within and above the floor of the outer tray, and at least one device located on the inner organizing tray, in which the inner organizer tray is encircled with at least one band of shrink-wrap material, the encircled inner organizer tray is within and suspended above the floor of the outer tray, and the shrink-wrap film is shrunken around at least one device.

2. The container of claim 1 in which a plurality of devices are held by a single band of shrink-wrap film.

3. The container of claim 1 in which a single device is held by a plurality of bands of shrink-wrap film.

4. The container of claim 1 in which a plurality of devices are held by plurality of bands of shrink-wrap film.

5. The container of claim 4 in which the number of devices is equal to the number of bands of shrink-wrap film.

6. The container of claim 1 in which at least one device is completely surrounded by a closed volume of shrink-wrap film.

7. The container of claim 1 in which at least one device is encircled by an open volume of shrink-wrap film.

8. The container of claim 7 in which at the open volume of shrink-wrap film is open at least one end.

9. The container of claim 8 in which the open volume of shrink-wrap film is open at two opposite ends.

10. The container of claim 9 in which an inner organizer tray is located at one end of the outer tray.

11. The container of claim 1 further comprising a. a sealable lid configured to engage the outer tray.

12. The container of claim 11 further comprising adhesive sufficient to create a hermetic seal between the sealable lid and the outer tray.

13. A method of packaging at least one device, comprising the steps of:

a) providing an inner organizing tray, an outer tray having a floor and a means to suspend the inner organizing tray within and above the floor of the outer tray, b) locating at least one device on the inner organizing tray, c) encircling the inner organizer tray with at least one band of shrink-wrap material, d) placing the encircled inner organizer tray within and suspended above the floor of the outer tray, and e) shrinking the shrink-wrap film around at least one device.

14. The method of claim 11, further comprising the step of locating at least one additional device within an intermediate space defined between the floor of the outer tray and the inner organizer tray.

15. The method of claim 11, in which step a) comprises providing the inner organizer tray in a configuration which permits it to be mounted on a equipment support platform, and in which step b) comprises locating at least one device on the inner organizing tray such that at least one device is arranged for use on the mounted inner organizing tray.

* * * * *